(12) United States Patent
Tomlin et al.

(10) Patent No.: US 9,200,194 B2
(45) Date of Patent: Dec. 1, 2015

(54) FLUID CONVEYING CONDUIT

(71) Applicant: Ecoluminaire Limited, Ruddington (GB)

(72) Inventors: Russell Stephen Tomlin, Toton (GB); James Raymond Malloy, Jr., Orlando, FL (US)

(73) Assignee: Ecoluminaire Limited, Ruddington, Nottingham (GB)

( * ) Notice: Subject to any disclaimer, the term of this patent is extended or adjusted under 35 U.S.C. 154(b) by 0 days.

(21) Appl. No.: 13/797,899

(22) Filed: Mar. 12, 2013

(65) Prior Publication Data
US 2013/0192598 A1    Aug. 1, 2013

Related U.S. Application Data

(63) Continuation of application No. 12/303,463, filed as application No. PCT/GB2006/002059 on Jun. 5, 2006, now Pat. No. 8,443,845.

(51) Int. Cl.
| | | |
|---|---|---|
| *C09K 11/00* | (2006.01) | |
| *A61B 19/00* | (2006.01) | |
| *A61M 16/00* | (2006.01) | |
| *A61M 16/08* | (2006.01) | |

(52) U.S. Cl.
CPC .............. *C09K 11/00* (2013.01); *A61B 19/54* (2013.01); *A61M 16/00* (2013.01); *A61M 16/0875* (2013.01); *A61B 2019/5441* (2013.01); *A61M 2202/0208* (2013.01); *A61M 2205/584* (2013.01); *A61M 2205/587* (2013.01)

(58) Field of Classification Search
USPC .............. 264/632, 506, 508, 512, 563, 573
See application file for complete search history.

(56) References Cited

U.S. PATENT DOCUMENTS

| | | | |
|---|---|---|---|
| 2,839,088 A | 6/1958 | Biklen | |
| 4,275,768 A | 6/1981 | Riggs et al. | |
| 4,410,012 A | 10/1983 | Redding et al. | |
| 4,662,404 A * | 5/1987 | LeVeen et al. | ............... 138/120 |
| 4,759,453 A | 7/1988 | Paetzold | |
| 4,832,214 A * | 5/1989 | Schrader et al. | ............. 215/11.1 |
| 5,027,741 A | 7/1991 | Smith et al. | |
| 5,111,605 A | 5/1992 | Bossi | |

(Continued)

FOREIGN PATENT DOCUMENTS

| | | |
|---|---|---|
| WO | WO 01/47438 | 7/2001 |
| WO | WO 02/19918 | 3/2002 |

(Continued)

OTHER PUBLICATIONS

PCT International Patent Application No. PCT/GB2006/002059, filed Jun. 5, 2006.

(Continued)

*Primary Examiner* — Stella Yi
(74) *Attorney, Agent, or Firm* — Craig R. Miles; CR Miles P.C.

(57) ABSTRACT

A fluid-containing conduit (10,30,40,50) including at least one luminescent marker (14) whereby the fluid-containing conduit is visible in a low light condition. The marker may be in the form of one or more elongate ribs (16) containing luminescent material along interior wall surface (18), or may be elongate luminescent bands (52,54) adjacent the exterior wall (20) of the conduit, or may be indicia containing luminescent material such as ink (42).

14 Claims, 5 Drawing Sheets

(56) References Cited

U.S. PATENT DOCUMENTS

| | | | |
|---|---|---|---|
| RE34,701 E | 8/1994 | Goodman | |
| 5,921,978 A | 7/1999 | Thompson et al. | |
| 5,983,949 A | 11/1999 | Pohle | |
| 6,059,768 A * | 5/2000 | Friedman | 604/523 |
| 6,092,558 A | 7/2000 | Maccario | |
| 6,183,102 B1 | 2/2001 | Mortz et al. | |
| 6,189,574 B1 | 2/2001 | Iwasaki et al. | |
| 6,257,734 B1 | 7/2001 | Tchira | |
| 6,354,331 B1 | 3/2002 | Fisher et al. | |
| 6,574,497 B1 | 6/2003 | Pacetti | |
| 6,631,819 B1 * | 10/2003 | Diak/Ghanem | 215/11.1 |
| 7,785,514 B2 | 8/2010 | McCarthy | |
| 7,878,222 B2 | 2/2011 | Weisel | |
| 2002/0029032 A1 | 3/2002 | Arkin | |
| 2004/0253186 A1 | 12/2004 | Maillan et al. | |
| 2004/0253281 A1 | 12/2004 | Herweck et al. | |
| 2005/0171492 A1 | 8/2005 | Rodriquez | |
| 2006/0258982 A1 | 11/2006 | Powell et al. | |
| 2007/0292477 A1 * | 12/2007 | Kumar | 424/429 |
| 2010/0006171 A1 | 1/2010 | Tomlin et al. | |
| 2010/0261946 A1 | 10/2010 | Kaplan | |

FOREIGN PATENT DOCUMENTS

| | | |
|---|---|---|
| WO | WO 03/075979 | 9/2003 |
| WO | WO 2004/064891 | 8/2004 |
| WO | WO 2007/141463 | 12/2007 |

OTHER PUBLICATIONS

International Search Report for PCT/GB2006/002059 dated Jan. 26, 2007.

Corresponding European Patent Application No. 06 744 113.9; Office Action mailed Jan. 20, 2015, 4 total pages.

* cited by examiner

FLUID CONVEYING CONDUIT

CROSS-REFERENCE TO RELATED APPLICATION

This United States Patent Application is a continuation of U.S. patent application Ser. No. 12/303,463, filed Oct. 2, 2009, which is the United States National Stage of International Patent Cooperation Treaty Patent Application No. PCT/GB2006/002059, filed Jun. 5, 2006, each hereby incorporated by reference herein

FIELD OF THE INVENTION

This invention relates to a fluid conveying conduit and, in particular, a medical tube for administering fluids.

BACKGROUND OF THE INVENTION

In a low light condition it is often almost impossible to see a conventional tube or other fluid conveying conduit. As a result a user can find it difficult to locate the conduit if, for example, he wishes to move the conduit or engage and/or disengage a component from the conduit.

In addition, because conventional conduits are difficult to see in low light conditions it can be difficult for a person to avoid such a conduit if, e.g. it lies across his path, in a low light condition.

This is particularly so for medical tubes which may be used to provide a person with a continuous supply of oxygen, or to administer drugs to a person, while he is resident in a medical facility or at home.

In order for the person to move around, the length of medical tubing extending between the person and the dispensing station is often long, especially when a person needs to move from one room to another. As a result, lengths of medical tubing typically lie along the floor in several areas of the medical facility or home.

As mentioned, such medical tubing is almost impossible to see in low light conditions and so represents a major trip hazard since it is difficult for patients and carers to avoid.

As a result many patients and carers suffer falls, some fatal, as a result of tripping over a length of medical tube.

Therefore, there is a need for an improved fluid conveying conduit which helps to overcome the aforementioned problems.

BRIEF SUMMARY OF THE INVENTION

According to a first aspect of the invention there is provided a fluid conveying conduit comprising a conduit body including at least one luminescent marker, whereby the fluid conveying conduit is visible in a low light condition.

Rendering the fluid conveying conduit visible in a low light condition makes it easier for users and their carers to avoid the conduit, thereby reducing the likelihood of a trip occurring.

In one embodiment of the invention the conduit body defines a medical tube for administering fluids.

Preferably the or each luminescent marker includes an elongate, luminescent rib extending along the length of the conduit body, the or each elongate rib including a luminescent pigment. The provision of at least one elongate, luminescent rib means that the entire length of conduit is visible in a low light condition. An elongate rib is also readily manufacturable, e.g. by extrusion.

Optionally at least one elongate rib lies adjacent to an inner surface of the conduit body. Such a rib helps to reduce the likelihood of the tube kinking which might otherwise cut off the supply of fluid being administered to a user.

Alternatively at least one elongate rib lies adjacent to an outer surface of the conduit body. Such a feature provides a user or carer with a tactile identifier which could, for example allow him to readily identify the fluid being administered by a given medical tube.

Preferably the or each luminescent marker includes an elongate, luminescent band lying within the conduit body and extending along the length thereof, the or each elongate band including a luminescent pigment. Such an arrangement isolates the or each elongate band from the inner surface of the conduit body, thereby avoiding the possibility of the luminescent pigment adversely reacting with the fluid being conveyed.

In a preferred embodiment of the invention at least one portion of one or more of the elongate bands is coterminous with an outer surface of the conduit body. This arrangement is readily manufacturable while ensuring a desired amount of one or more elongate bands is visible.

The luminescent marker may also include an ink lying on a surface of the conduit body, the ink including a luminescent pigment. Such a feature allows the luminescent marker to be readily applied to a surface of the conduit body, by a method such as printing, in a range of differing configurations and graphical arrangements. In this way the luminescent marker may provide additional information, e.g. relating to the contents of the conduit, as well as rendering the conduit visible in a low light condition.

The conduit body may also include one or more dyes or secondary pigments so as to emit or reflect incident light in a predetermined range of wavelengths. In this way the conduit body is observed to have a particular colour which may be used to identify the fluid being administered by the conduit.

In a preferred embodiment the conduit body may include a translucent portion. This allows a user or carer to observe the contents of the conduit, while the conduit body also provides the aforementioned colour-based identification.

Alternatively the conduit body includes a transparent portion so that a user or carer is able to observe the contents of the conduit.

In another preferred embodiment, the conduit body includes a luminescent pigment. This allows the whole conduit body to define a luminescent marker, thereby providing the desired visibility in a low light condition.

In a further preferred embodiment, the luminescent pigment may be or include a phosphorescent pigment. Such pigments glow for a period after exposure to light.

Optionally the luminescent pigment includes one or more dyes or secondary pigments so as to emit light in a predetermined range of wavelengths. In this way the or each luminescent marker is observed to have a particular colour in a low light condition. The colour could then be used to identify the fluid being, e.g. administered by the conduit. Such identification is particularly useful in situations where several different conduits are used to administer different drugs to the same person. The ability of, e.g. a carer, to readily identify, in a low light condition, the fluid being administered by a particular conduit would help to ensure that each drug is injected into the correct conduit. Preferably the conduit body includes an antimicrobial additive. This can help to reduce the transmission of organisms such as MRSA (methicillin resistant *Staphylococcus aureus*) by the conduit, thereby reducing the risk of a conduit user developing an infection.

BRIEF DESCRIPTION OF THE DRAWINGS

There now follows a brief description of preferred embodiments of the invention, by way of non-limiting examples, with reference being made to the accompanying drawings in which.

DETAILED DESCRIPTION OF THE INVENTION

Figure 1:
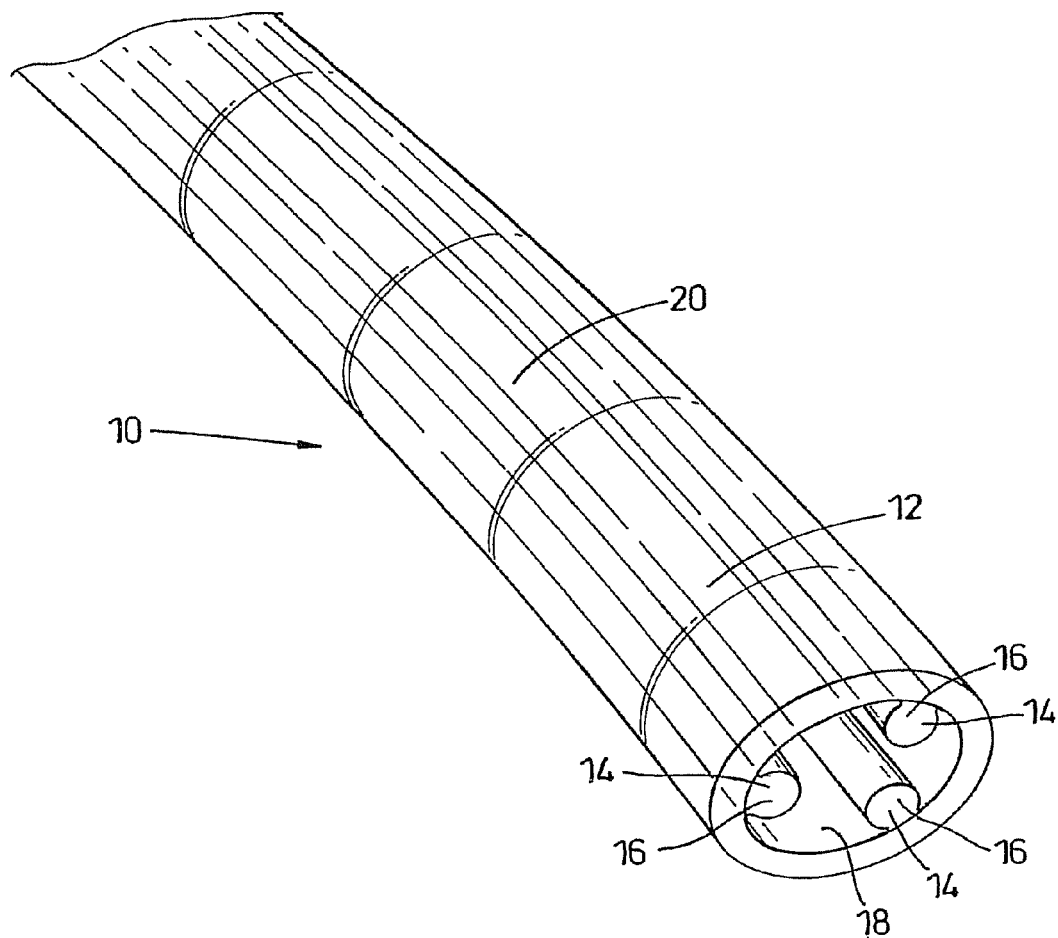
FIG. 1 shows a section of medical tube according to a first embodiment of the invention.
Figure 2:
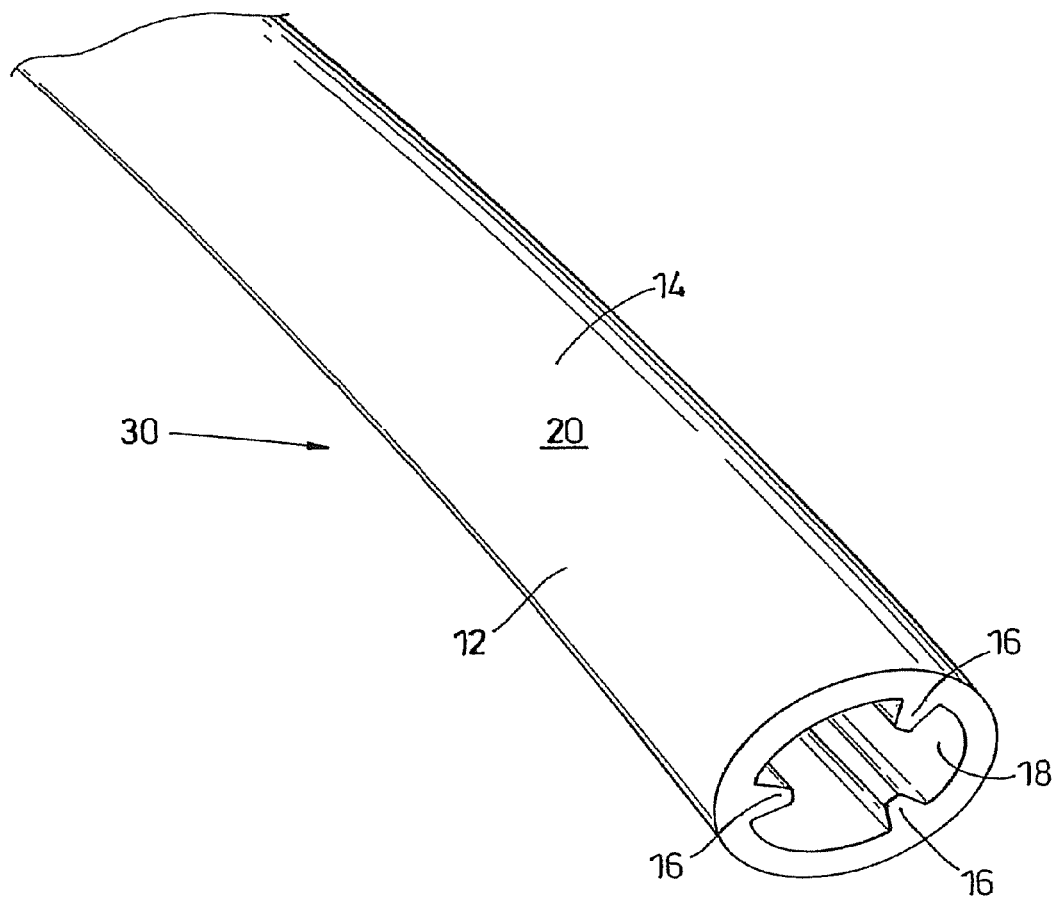
FIG. 2 shows a section of medical tube according to a second embodiment of the invention.
Figure 3:
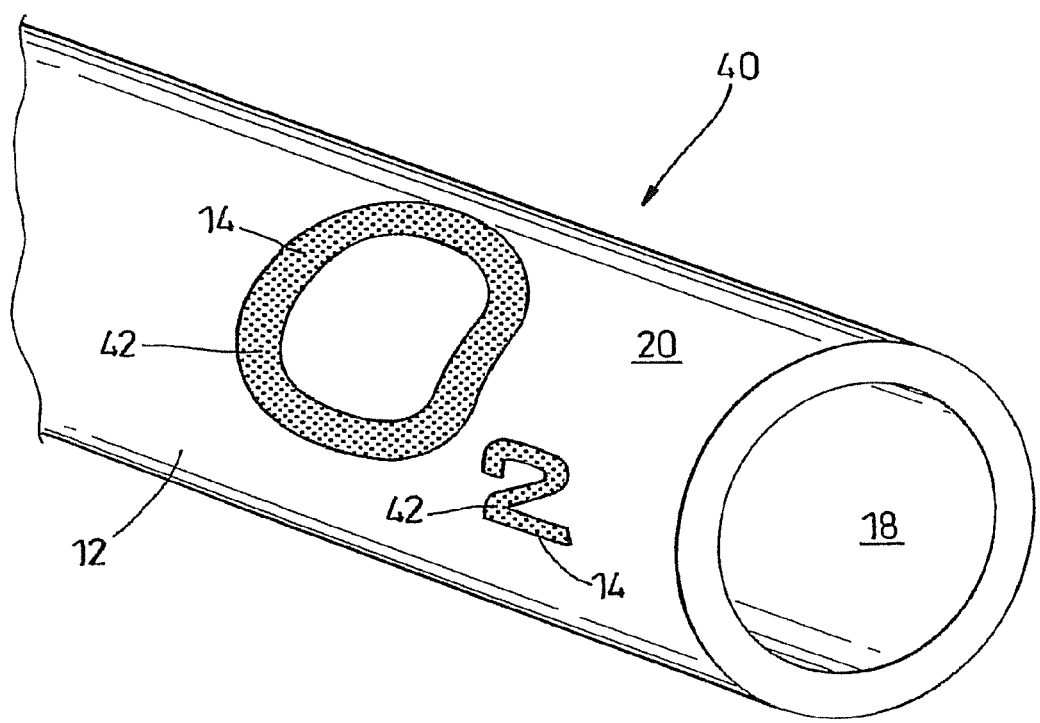
FIG. 3 shows a section of medical tube according to a third embodiment of the invention.

In the drawings, like numerals indicate like elements throughout. Certain terminology is used herein for convenience only and is not to be taken as a limitation on the present invention. The embodiments illustrated below are not intended to be exhaustive or to limit the invention to the precise form disclosed. These embodiments are chosen and described to best explain the principle of the invention and its application and practical use and to enable others skilled in the art to best utilize the invention.

A fluid conveying conduit according to a first embodiment of the invention is designated generally by the reference numeral 10, as shown in FIG. 1.

The fluid conveying conduit 10 comprises a conduit body 12 which defines a medical tube for administering fluids. The conduit body 12 includes three luminescent markers 14. Each luminescent marker 14 includes an elongate, luminescent rib 16 which extends along the length of the conduit body 12. Each elongate rib 16 includes a luminescent pigment (not shown). In a preferred embodiment the luminescent pigment is a phosphorescent pigment. A particularly preferred phosphorescent pigment is alkaline earth metal silicate aluminate.

Figure 4:
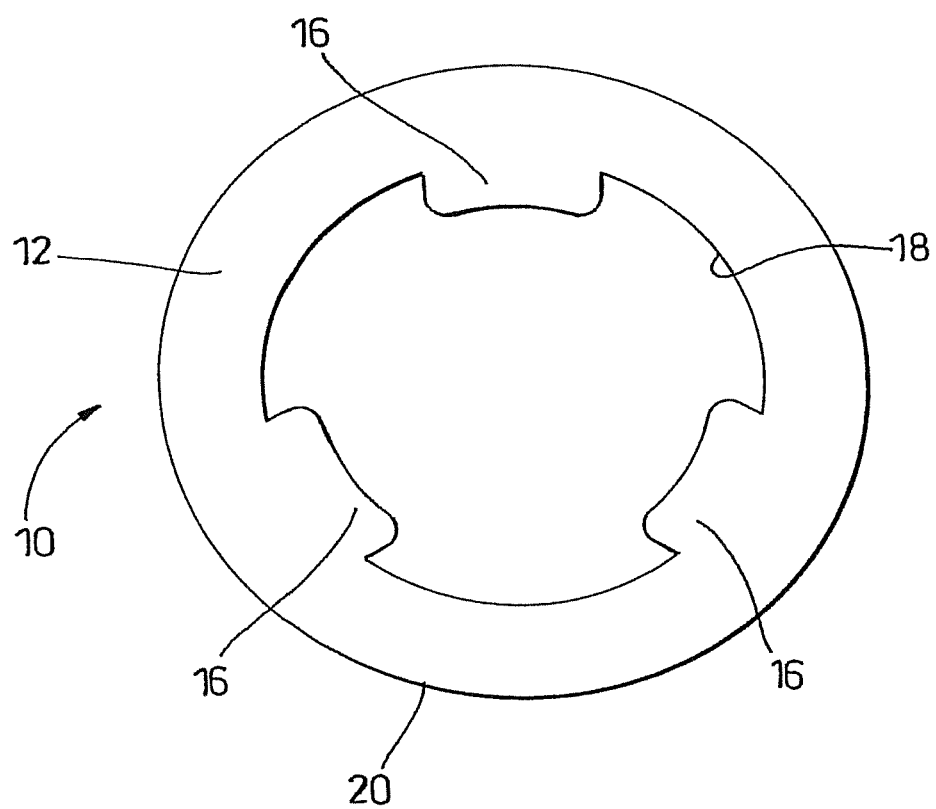
FIG. 4 shows a cross-sectional view through a section of medical tube according to the first embodiment of the invention.

In the embodiment shown, all three elongate ribs 16 lie adjacent to an inner surface 18 of the conduit body 12, as shown in FIG. 4. The elongate ribs 16 are equally spaced from one another around the inner surface 18 of the conduit. In other embodiments, of the invention one or more elongate ribs 16 may lie adjacent to an outer surface 20 of the conduit body 12. In addition, other embodiments of the invention may include different numbers and arrangements of elongate ribs 16. Furthermore, different shapes of cross-sectional profile are also possible.

In a low light condition, i.e. typically less than 1 lumen, each elongate rib 16 emits light so as to render the conduit visible to a user or carer. Each elongate rib 16 is able to emit visible light for many hours without the need for an external power source.

In the embodiment shown in FIG. 1, the entire conduit body 12 is transparent which means a user or carer is able to see the contents of the conduit 10. One type of polymer from which it is convenient to make the conduit body 12 is PVC.

In other embodiments, not shown, the conduit body 12 may include one or more dyes or secondary pigments so as to emit or reflect incident light in a predetermined range of wavelengths. In this way it is possible to provide a translucent conduit body 12 which has a predetermined tint, so as to provide a visible indication of what fluid is being administered by the tube 10. A desirable level of translucency, or tinting, is 5% as this provides a suitable visible indication while still allowing the contents of the conduit 10 to be seen.

The luminescent pigment in one or more elongate ribs 16 may also include one or more dyes or secondary pigments. In such embodiments, each elongate rib 16, in use, emits light of a particular colour. This provides a visible indication of what fluid is being administered by the conduit 10 in a low light condition.

A fluid conveying conduit according to a second embodiment of the invention is designated generally by the reference numeral 30. The second fluid conveying conduit 30 shares many features with the first fluid conveying conduit 10. These common features are designated by the same reference numerals.

The second fluid conveying conduit 30 includes an opaque conduit body 12 which defines a medical tube, and has three elongate ribs 16 integrally moulded therewith. Each elongate rib 16 extends along the length of the conduit body 12.

The conduit body 12 and each elongate rib 16 includes a luminescent pigment (not shown). Consequently, in a low light condition, the whole conduit 30 emits light so as to render it visible.

A fluid conveying conduit according to a third embodiment of the invention is designated generally by the reference numeral 40. The third fluid conveying conduit 40 shares many features with the first and second fluid conveying conduits 10, 30. These common features are designated by the same reference numerals.

The third medical tube 40 includes a conduit body 12 which defines a medical tube, and may be transparent, translucent or opaque.

An ink 42 which includes a luminescent pigment (not shown) lies on the outer surface 20 of the conduit body 12. The ink 42 is arranged as a graphic symbol which assists a user or carer in identifying the fluid being carried by the conduit 40. In the example shown, the graphic "$O_2$" is printed on the outer surface 20. Other embodiments may include different graphics and/or arrangements of ink 42.

In a low light condition, the ink 42 glows, thereby allowing a user or carer to see the conduit 40 as well as readily identify the contents, i.e. oxygen.

A fluid conveying conduit according to a fourth embodiment of the invention is designated generally by the reference numeral 50. The fourth fluid conveying conduit 50 shares many features with the first, second and third fluid conveying conduits 10, 30, 40. These common features are designated by the same reference numerals.

The fourth medical tube 50 includes a conduit body 12 which defines a medical tube, and is transparent. In other embodiments, the conduit body 12 may be translucent or opaque.

Figure 5:
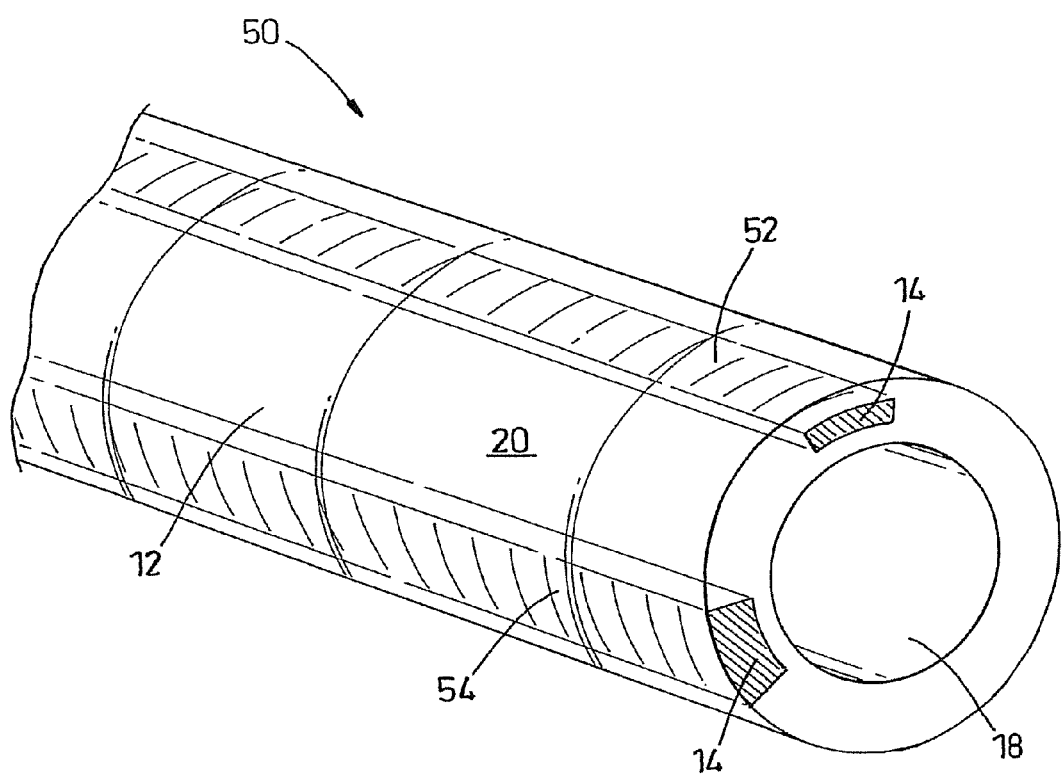
FIG. 5 shows a section of medical tube according to a fourth embodiment of the invention.

The conduit body 12 includes two luminescent markers 14, each of which includes an elongate, luminescent band 52, 54 that lies within the conduit body 12 and extends along the length thereof, as shown in FIG. 5. Each elongate band 52, 54 includes a luminescent pigment (not shown). The cross-sectional shape of each elongate band 52, 54 may differ from that shown in FIG. 5. For example, in other embodiments the or each elongate band 52, 54 could have a circular, oval, elliptical, oblong or square cross-sectional shape.

A first elongate band 52 lies completely within the conduit body 12, whereas one portion of a second elongate band 54 is coterminous with the outer surface 20 of the conduit body 12.

In a low light condition, each of the elongate bands 52, 54 emits light along substantially the entire length of the conduit body 12, thereby rendering the whole length of conduit 50 visible.

A fluid conveying conduit according to a fifth embodiment of the invention (not shown) has a conduit body 12 which defines a medical tube, and includes an antimicrobial additive. In this way the fourth conduit is also able to inhibit the spread of infection within a medical facility or home.

Whilst the examples described above relate to medical tubing, it is envisaged that the invention could be applied to other fluid conveying conduits such as hoses and pipes.

We claim:

1. A method of producing a fluid conveying conduit, said method comprising:
   providing an elongate conduit body having a translucent portion; and
   integrally disposing at least one elongate rib adjacent an inner surface of said elongate conduit body;
   said at least one elongate rib projecting outwardly from said inner surface and continuously extending along an entire length of said elongate conduit body;
   said at least one elongate rib including a luminescent pigment sufficient to render said entire length of said elongate conduit body visible in a low light condition.

2. The method of claim 1, further comprising providing said elongate conduit body with one or more dyes or secondary pigments which emit or reflect incident light in a predetermined range of wavelengths.

3. The method of claim 2, further comprising providing said elongate conduit body with a transparent portion.

4. The method of claim 1, further comprising providing said elongate conduit body with said luminescent pigment.

5. The method of claim 4, wherein said luminescent pigment comprises a phosphorescent pigment.

6. The method of claim 1, wherein said luminescent pigment further includes one or more dyes or secondary pigments which emit light in a predetermined range of wavelengths.

7. The method of claim 1, further comprising providing said elongate conduit body with an antimicrobial additive.

8. A method of producing a fluid conveying conduit, said method comprising:
   providing an elongate conduit body having a translucent portion; and
   embedding at least one elongate band within a wall of said elongate conduit body to continuously extend along an entire length of said elongate conduit body;
   said at least one elongate band including a luminescent pigment sufficient to render said entire length of said elongate conduit body visible in low light.

9. The method of claim 8, further comprising configuring said at least one elongate band to have a portion coterminous with an outer surface of said elongate conduit body.

10. The method of claim 8, further comprising providing said elongate conduit body with one or more dyes or secondary pigments which emit or reflect incident light in a predetermined range of wavelengths.

11. The method of claim 8, further comprising providing said elongate conduit body with a transparent portion.

12. The method of claim 8, further comprising providing said elongate conduit body with said luminescent pigment.

13. The method of claim 12, wherein said luminescent pigment comprises a phosphorescent pigment.

14. The method of claim 8, further comprising providing said elongate conduit body with an antimicrobial additive.

* * * * *